US006534676B2

(12) United States Patent
Morkin et al.

(10) Patent No.: US 6,534,676 B2
(45) Date of Patent: Mar. 18, 2003

(54) METHOD TO TREAT CHRONIC HEART FAILURE AND/OR ELEVATED CHOLESTEROL LEVELS USING 3,5-DIIODOTHYROPROPIONIC ACID AND METHOD TO PREPARE SAME

(75) Inventors: Eugene Morkin, Tucson, AZ (US); Gregory D. Pennock, Tucson, AZ (US); Joseph J. Bahl, Tucson, AZ (US); Steven Goldman, Tucson, AZ (US)

(73) Assignees: The Arizona Board of Regents on Behalf of the University of Arizona, Phoenix, AZ (US); Southern Arizona Veterans Affairs Health Care System, Tucson, AZ (US)

( * ) Notice: Subject to any disclaimer, the term of this patent is extended or adjusted under 35 U.S.C. 154(b) by 0 days.

(21) Appl. No.: 09/774,994

(22) Filed: Jan. 31, 2001

(65) Prior Publication Data

US 2002/0151594 A1 Oct. 17, 2002

(51) Int. Cl.$^7$ ............................................. C07C 63/00

(52) U.S. Cl. ........................ 562/405; 514/557; 514/568

(58) Field of Search ..................... 562/405; 514/557, 514/568

(56) References Cited

U.S. PATENT DOCUMENTS

| | | | |
|---|---|---|---|
| 2,803,654 A | 8/1957 | Anthony et al. | ............. 260/519 |
| 5,158,978 A | 10/1992 | Rubin | ......................... 514/567 |
| 5,284,971 A | 2/1994 | Walker et al. | ............... 562/429 |
| 5,883,294 A | 3/1999 | Scanlan et al. | ............. 562/471 |

OTHER PUBLICATIONS

Deirdre M. B. Hickey et al, "Synthesis of Thyroid Hormone Analogues. Part 3. Iodonium Salt Approaches to SK&F L–94901", J. Chem. Soc., Perkin Trans. I, (1988), pp. 3103–3111.*
Blank B, Pfeiffer FR, Greenburg CM, Kerwin JF, Thyromimetics. I., The synthesis and hypocholesteremic activity of some 3' and 3', 5'–Alryl and Aryl–3,5–Diiododthyronines, J Med Chem 1963; 6:554–560.
Blank B, Pfeiffer FR, Greenberg CM, Kerwin JF, Thyromimetics. II., The Synthesis and Hypocholesteremic Activity of Some b–Diethylaminoethyl esters of Iodinated Thyroalkanoic Acids, J Med Chem 1963;560–563.
Leeson PD, Ellis D, Emmett JC, Shah VP, Showell GA, Underwood AH, Thyroid Hormone Snalogues. Synthesis of 3'–Substituted 3,5–Diiodo–L–Thyronines and Quantitative Structure–Activity Studies of in Vitro and in Vivo Thyromimetic Activities in Rat Liver and Heart, J Med Chem 1988;31:37–54.
Hamilton MA, Stevenson LW, Fonarow GC, Steimle A, Goldhaber JI, Child JS, Chopra IJ, Moriguchi JD, Hage A.

Safety and hemodynamic effect of Intravenous triiodothyronine in advanced congestive heart failur, Am J Cardiol 1998;81:443–47.
Moruzzi P, Doria E, Agostoni PG, Capacchione V, Sganzerla, PG, Usefulness of L–Thyroxine to Improve Cardiac and Exercise Performance in Dilated Cardiomyopathy, Am J Cardiol 1994;73:374–78.
Moruzzi P, Doria E, Agostoni PG, Medium–Term Effectiveness of L–Tyroxine Treatment in Idiopathic Dilated Cardiomyopathy, Am J Med 1996;101:461–7.
Pennock GD, Raya TE, Bahl JJ, Goldman S, Morkin E, Cardiac Effects of 3,5–Diiodothyropropionic Acid, a Thyroid Hormone Analog with Inotropic Selectivity, J Pharmacol Exp Ther 1992;263:163–9.
Mahaffey KW, Raya TE, Pennock GD, Morkin E, Goldman S., Left Ventricular Performance and Remodeling in Rabbits After Myocardial Infarction. Effects of a Thyroid Hormone Analogue, Circulation 1995;91:794–801.
Pennock GD, Raya TE, Bahl JJ, Goldman S, Morkin E., Combination Treatment with Captopril and the Thyroid Hormone Analogue, 3,5–Diiodothyropropionic Acid. A New Approach to Improving Left Ventricular Performance in Heart Failure, Circulation 1993;88:1289–98.
Goldman S, Olajos M, Morkin E., Control of Cardiac Output in Thyrotoxic Calves. Evaluation of Changes in Systemic Circulation, J Clin Invest 1984;73:358–65.
Asanoi H, Ishizaka S, Joho S, Kameyama T, Inoue H, Sasayama S., Altered Inotropic and Lusitropic Responses to Heart Rate in Conscious Dogs with Tachycardia Induced Heart Failure, J Am Coll Cardiol 1996;27:728–35.
Mulieri LA, Hasenfuss G, Leavitt B, Allen PD, Alpert NR., Altered Myocardial Force–Frequency Relation in Human Heart Failure, Circulation 1992;85:1743–50.
13. Litwin SE, Zhang D, Roberge P, Pennock GD., DITPA Prevents the Blunted Contraction–Frequency Relationship in Myocytes from infarcted Hearts, Am J Physiol (Heart and Circ Physiol) 2000;278:H862–70.
Khoury SF, Hoit BD, Vrushank D, Pawloski–Dahm CM, Shao Y, Gabel M, Periasamy M, Walsh RA, Effects of Thyroid Hormone on Left Ventricular Performance and Regulation of Contractile and Ca2+ Cycling Proteins in the Baboon. Implications for the Force–Frequency and Relaxation–Frequency Relationship, Circ Res 1996;79:727–35.
Hoit BD, Pawloski–Dahm CM, Shao Y, Gabel M, Walsh RA, The Effects of a Thyroid Hormone Analog on Left Ventricular Performance and Contractile and Calcium Cycling Proteins in the Baboon, Proc Assoc Am Physicians 1997; 109:136–45.

(List continued on next page.)

Primary Examiner—Paul J. Killos
(74) Attorney, Agent, or Firm—Hayes Soloway P.C.

(57) ABSTRACT

Applicants' invention includes a method to treat a patient having congestive heart failure by administering a therapeutically effective amount of 3,5-diidothyropropionic acid. Applicants' invention further includes a method to lower cholesterol blood levels of a patient by administering a therapeutically effective amount of 3,5-diidothyropropionic acid. Applicants' invention further includes a synthetic method to prepare 3,5-diidothyropropionic acid.

20 Claims, No Drawings

OTHER PUBLICATIONS

Tomanek RJ, Zimmerman MB, Survarna PR, Morkin E, Pennock GD, Goldman S., A Thyroid Hormone Analog Stimulates Angiogenesis in the Post Infarction Rat Heart, J Mol Cell Cardiol 1998;30:923–32.

Matsuura T., Synthesis of 3,5,3',5'Hhalogen–Substituted Thyropropionic Aacids, J Med Chem 1964;830–831.

Morken, et al., "Studies on the Use of Thyroid Hormone and a Thyroid Hormone Analogue in the Treatment of Congestive Heart Failure", The Society of Thoracic Surgeons, 1993, Sections 54–60.

Pennock, et al., "Combination Treatment with Captopril and the Thyroid Hormone Analogue 3,5–Diiodothyropropionic Acid", Circulation, 1993, pp. 1289–1298.

Mahaffey, et al., "Left Ventricular Performance and Remodeling in Rabbits after Myocardial Infarction", American Heart Association, 1994, pp. 794–801.

Morkin, et al., "Development of a Tyroid Hormone Analogue for the Treatment of Congestive Heart Failure", Symposium on Novel Actions of Thyroid Hormone, 1996, pp. 521–526.

Spooner, et al., "Thyroid Hormone and Thyroid Hormone Analogues in the Treatment of Heart Failure", Lippincott Williams & Wilkins, 1999, pp. 395–399.

Pennock, et al., "Prevention of Abnormal Sarcoplasmic Reticulum Calcium Transport and Protein Expression in Post–infarction Heart Failure Using 3,5–Diiodothyropropionic Acid (DITPA)", Academic Press, 2000, pp. 1939–1953.

* cited by examiner

US 6,534,676 B2

METHOD TO TREAT CHRONIC HEART FAILURE AND/OR ELEVATED CHOLESTEROL LEVELS USING 3,5-DIIODOTHYROPROPIONIC ACID AND METHOD TO PREPARE SAME

FIELD OF THE INVENTION

The present invention relates to a treatment for patients having congestive heart failure and/or elevated cholesterol blood levels by administering a therapeutically effective amount of 3,5-Diiodothyropropionic acid. The present invention further relates to a synthetic method to prepare 3,5-Diiodothyropropionic acid.

BACKGROUND OF THE INVENTION

Congestive heart failure continues to be a major health problem, affecting about 4.6 million people in the United States, and its prevalence is predicted to increase over the next several decades. The magnitude of heart failure as a clinical problem has placed emphasis on the need to develop new treatment strategies.

One approach that has emerged is the use of thyroid hormone, which has unique physiologic and biochemical actions that make it a novel and potentially useful agent for treatment of heart failure. Thyroid hormone has been shown to act at the transcriptional level on the content of myocardial calcium cycling proteins to stimulate calcium uptake by sarcoplasmic reticulum. In addition, thyroid hormone causes a reciprocal shift in cardiac myosin heavy chain (MHC) isoform expression, increasing the expression of the high activity $V_1$ isoform and decreasing the low activity $V_3$ form. These biochemical alterations may underlie the ability of thyroid hormone to increase the rates of ventricular pressure development and relaxation.

Thyroid hormones include the L-forms of thyroxine (3,5, 3'5'-L-thyronine; hereinafter thyroxine or $T_4$) and triiodothyronine (3',3,5-L-triiodothyrone; hereinafter triiodothyronine or $T_3$). 3',5',3-L-Triiodothyronine (hereinafter Reverse $T_3$ or r $T_3$), is a normal metabolite of $T_4$. $T_4$ is synthesized in the thyroid gland and is the circulating form of hormone found in plasma. Although small amounts of $T_3$ are synthesized by the thyroid gland, the majority is formed from the metabolism of thyroxine in peripheral tissues by the enzyme 5'-monodeiodinase. The molecular basis for the actions of thyroid hormones is though to be mediated through the binding of $T_3$ to chromatin-bound nuclear receptors. There are two major subtypes of the thyroid hormone receptor, TRα and TRβ, which are the products of two different genes. These genes are members of the c-erbA protooncogene family and are related to a large number of steroid and peptide hormone receptors collectively known as the steroid-thyroid hormone superfamily. The TR α andβ subtypes are differentially expressed in various tissues.

Thyroxine, synthesized by methods such as described in U.S. Pat. No. 2,803,654, is the principle thyroid hormone in current clinical use. This is largely because of its long half-life of 6–7 days. Triiodothyronine, which is less strongly bound to plasma proteins and has a more rapid onset of action, is available for intravenous administration. However, $T_3$ has a relatively short half-life of two days or less.

Numerous studies have been carried out to synthesize thyroid hormone analogs that mimic the actions of the natural hormones. The objective of most of these efforts has been to develop thyromimetics that lower plasma cholesterol without adverse cardiac effects. A series of thyroxine analogs and methods of synthesis are described in U.S. Pat. No. 3,109,023.

Thyroid hormone agonists that are highly selective for the thyroid hormone receptor β subtype are described in U.S. Pat. Nos. 5,883,294. 5,284,971 describes a class of thyromimetics, which have the distinguishing characteristic of a sulfonyl bridge in the diphenyl core.

A more recent development has been the use of thyroid hormones for the treatment of cardiovascular compromise. A method for the treatment of patients with sudden (acute) cardiovascular compromise by administration of thyroid hormone is described in U.S. Pat. No. 5,158,978. The method teaches administration of $T_4$ and $T_3$ after cardiac arrest by injection into a vein, a central venous catheter, into the pulmonary circulation or directly into the heart.

Short-term intravenous administration of $T_3$ to patients with advanced congestive failure has been shown to improve cardiac output and decrease arterial vascular resistance. Oral administration of L-thyroxine also has been shown to improve cardiac performance and exercise capacity in patients with idiopathic dilated cardiomyopathy when given for two weeks and 3 months. Although the number of patients in these studies was small, the results were generally favorable and established the basis for further investigation into the safety and potential benefits of treatment of heart failure with thyroid hormone or thyroid hormone analogs.

Because of potential adverse effects of thyroid hormone, such as metabolic stimulation and tachycardia, what is required are thyroid hormone analogs with fewer undesirable side effects. Applicants have found that 3,5-Diiodothyropropionic acid (DITPA) is a thyroid hormone analog that increases cardiac performance with approximately half of the chronotropic effect and less metabolic stimulation than L-thyroxine. Like thyroid hormone, DITPA binds to nuclear $T_3$ receptors of the c-erbA proto-oncogene family. DITPA has been shown to improve left ventricular (LV) performance in post-infarction experimental models of heart failure when administered alone or in combination with an angiotensin I-converting enzyme inhibitor.

In addition to its well-known chronotropic and inotropic actions on the heart, thyroid hormone decreases arterial resistance, venous resistance and venous compliance. The net effect of these changes is to increase cardiac output more than arterial pressure, resulting in decreased calculated arterial vascular resistance. When used in experimental models of heart failure DITPA acts similarly to thyroid hormone, affecting both the heart and the peripheral circulation. Loss of the normal increase in contractility with heart rate, referred to as the positive force-frequency relationship, has been reported both in failing human myocardium and in animal models of heart failure. DITPA administration prevents the flattened contraction-frequency relationship in single myocytes from infarcted rabbit hearts. DITPA improves myocyte function, enhances calcium transport in the sarcoplasmic reticulum (SR) and prevents the down regulation of SR proteins associated with post-infarction heart failure in rabbits. In normal primates, DITPA enhances the in vivo force-frequency and relaxation-frequency relationships in a manner similar to thyroid hormone. DITPA is able to bring about these hemodynamic changes without increasing cardiac mass appreciably or adversely affecting ventricular dimensions. A morphometric analysis indicates that in post-infarction rats treated with DITPA there is an increase in capillary growth in the border zone around the infarct.

SUMMARY OF THE INVENTION

Applicants have found that 3,5-Diiodothyropropionic acid (DITPA) is a thyroid hormone analog that increases cardiac performance with approximately half of the chronotropic effect and less metabolic stimulation than L-thyroxine. Like thyroid hormone, DITPA binds to nuclear $T_3$ receptors of the c-erbA proto-oncogene family. DITPA has been shown to improve left ventricular (LV) performance in post-infarction experimental models of heart failure when administered alone or in combination with an angiotensin I-converting enzyme inhibitor.

In addition to its well-known chronotropic and inotropic actions on the heart, thyroid hormone decreases arterial resistance, venous resistance and venous compliance. The net effect of these changes is to increase cardiac output more than arterial pressure, resulting in decreased calculated arterial vascular resistance.

When used in experimental models of heart failure DITPA acts similarly to thyroid hormone, affecting both the heart and the peripheral circulation. Loss of the normal increase in contractility with heart rate, referred to as the positive force-frequency relationship, has been reported both in failing human myocardium and in animal models of heart failure. DITPA administration prevents the flattened contraction-frequency relationship in single myocytes from infarcted rabbit hearts. In normal primates, DITPA enhances the in vivo force-frequency and relaxation-frequency relationships in a manner similar to thyroid hormone. DITPA is able to bring about these hemodynamic changes without increasing cardiac mass appreciably or adversely affecting ventricular dimensions. A morphometric analysis indicates that in post-infarction rats treated with DITPA there is an increase in capillary growth in the border zone around the infarct.

A dose-ranging study of DITPA was performed in seven normal volunteers. After establishing that the drug was well tolerated, a double-blind comparison of the effects of DITPA versus placebo was carried out in 19 patients with congestive failure.

DETAILED DESCRIPTION OF PREFERRED EMBODIMENTS

In overview, DITPA was synthesized following good manufacturing procedures by coupling dianisoleiodium trifluoroacetate with ethyl-3-(3,5-diiodo-4-hydroxyphenyl)-propionate followed by removal of the methyl and ethyl protective groups. This coupling strategy does not produce $T_3$ or $T_4$ as by products because the compound giving rise to the outer ring does not contain iodine and the side chain of the inner ring reactant lacks an amino group.

The structure of the DITPA prepared using this synthetic route was authenticated by proton magnetic resonance and its purity was checked by reverse phase HPLC. The principle impurity was identified as the ethyl ester of DITPA. Only batches of the final compound with greater than 95% purity were used in this study.

Applicants' synthesis of DITPA uses 3-(4-hydroxyphenyl)-propionic acid, compound I shown below, as a starting material. In a first synthetic step, compound I is reacted with potassium iodide/iodine, and then with methylamine, to form 3-(3,5-diiodo-4-hydroxyphenyl) propionic acid, compound II.

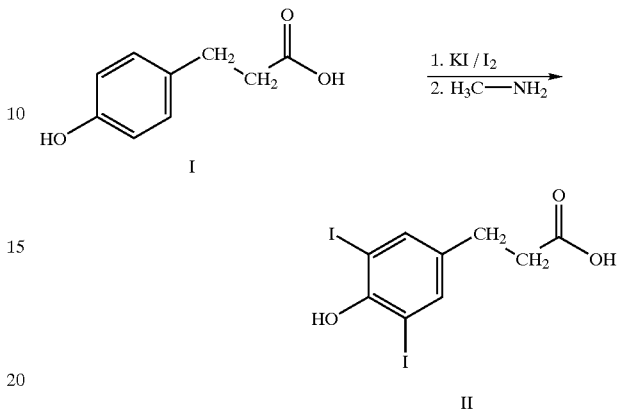

Compound II is next reacted with ethanol, using p-toluenesulfonic acid as a catalyst, to form ethyl-3-(3,5-diiodo-4-hydroxyphenyl)propionate, compound III.

Compound III is subsequently reacted with coupling agent dianisoleiodonium trifluoroacetate.

Coupling agent dianisoleiodonium trifluoroacetate is prepared by first reacting trifluoroacetic acid, compound IV, with red fuming nitric acid and iodine to form iodine(III) trifluoroacetate, compound V.

In a subsequent step, compound V is reacted with anisole, i.e. methoxybenzene, to form dianisoleiodonium trifluoroacetate, compound VI. Applicants use trifluoroacetate as the counterion in compound VI because use of other counterions results in compounds that are more hygroscopic, and therefore, likely have limited shelf lives.

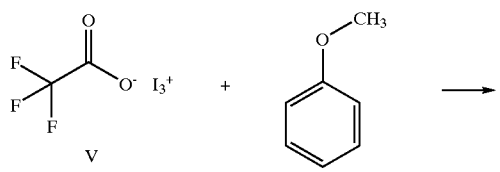

Ethyl-3-(3,5-diiodo-4-hydroxyphenyl)propionate, compound III, is next reacted with dianisoleiodonium trifluoroacetate, compound VI, to form ethyl-3-(4'-methoxy-3,5-diiodothyro) propionate, compound VII.

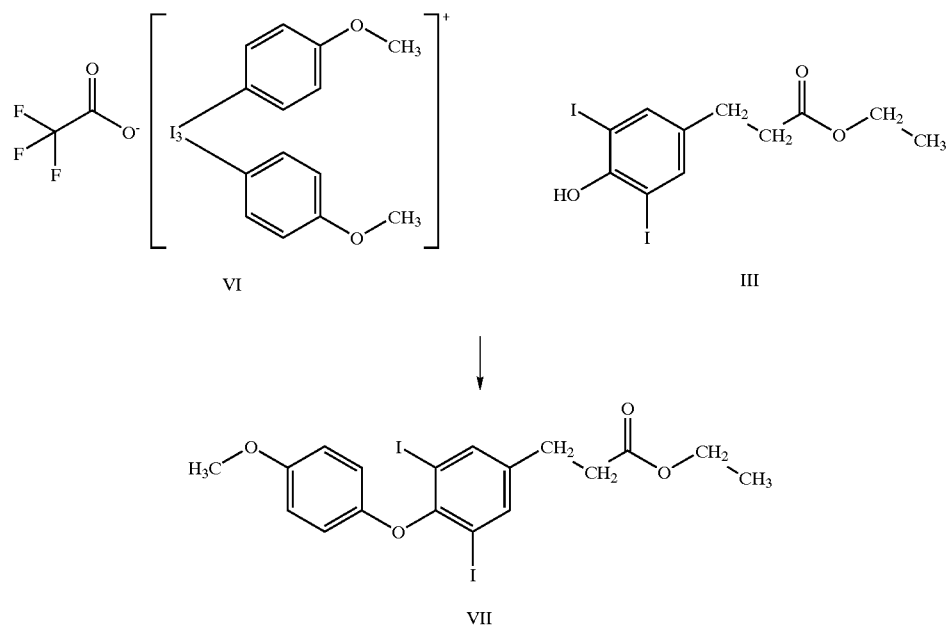

In the final step of Applicants' synthetic method, ethyl-3-(4'-methoxy-3,5-diiodothyro) propionate, compound VII, is reacted with hydrogen iodide and glacial acid to hydrolyze both the ethyl ester and the methyl ether to give DITPA.

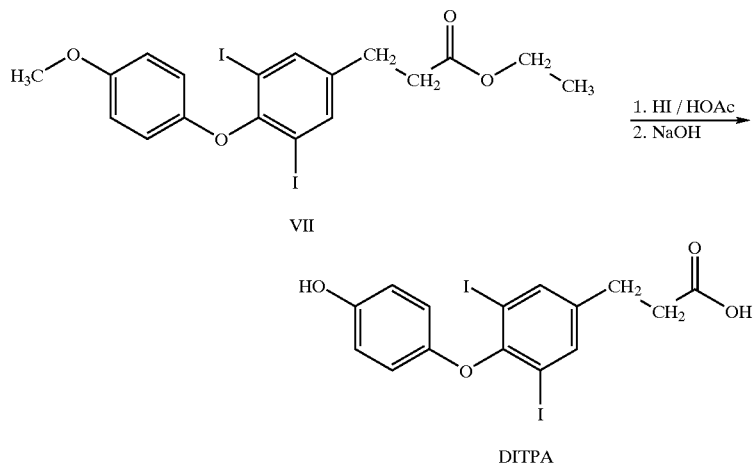

The following examples are presented to further illustrate to persons skilled in the art how to synthesize DITPA. These examples are not intended as limitations, however, upon the scope of Applicants' invention, which is defined only by the appended claims.

EXAMPLE 1

Synthesis of 3-(3,5-diiodo-4-hydroxyphenyl) propionic acid

Step 1: Weigh out 50 g of KI. Transfer to the pressure equalizing dropping funnel with a closed stopcock and add 60 ml of $H_2O$ and swirl until the salt is dissolved. Weigh 52 g of 12 and add to the dropping funnel, swirl until completely dissolved. Add 90 ml of $H_2O$ (total of 150 ml) and stopper the dropping funnel. Place in a secure location and go on to step 2.

Step 2: Weigh 16.2 g of 3-(4-hydroxyphenyl)-propionic acid and transfer into a 1.0 liter round bottom flask. Add a magnetic stir bar, 100 ml of 40% aqueous methylamine and 100 ml of $H_2O$. Stopper the flask. Clamp the flask above the magnetic stirrer and stir at a controlled rate until everything dissolves.

Step 3: Remove the stopper and replace it with the dropping funnel. Open the stopcock so that the iodine solution drips into the round bottom flask during a period of approximately 20 minutes. Allow the reaction to stir for 10 minutes after the addition is complete.

Step 4: Filter the reaction mixture, then pour into a 1 liter beaker and acidify with 2 N HCl (approximately 440 ml). Filter the resulting precipitate and rinse with cold $H_2O$. Cover the product with a piece of filter paper and dried overnight with suction.

Step 5 Recrystallize the product from ethanol. The ethanol has significant amounts of monoiodinated compound. Determine the product weight and melting point.

EXAMPLE 2

Synthesis of Ethyl-3-(3,5-diiodo-4-hydroxyphenyl) propionate

Step 1: Weigh 100 g of 3-(3,5-diiodo-4-hydroxyphenyl) propionic acid, transfer into a 500 ml round bottom flask, and add a magnetic stir bar. Add 15 ml of absolute ethanol and mix. Add 2.0 g of p-toluenesulfonic acid and then 150 ml of chloroform. Clamp the round bottom flask and place in the oil bath, but do not turn on the heat. Set up an Allihn condenser and a complete distillation assembly with a condenser to be cooled with recirculating ice water.

Step 2: With the recirculating pump running and a bucket of extra ice near by turn on the oil bath (setting 40 on the Variac). Adjust the Variac setting so that the distillation proceeds slowly (the total time for this esterification is 6–8 hours). After collecting 100 ml (approximately 2 hours) add an additional 15 ml of absolute ethanol and 100 ml of chloroform. When the next 100 ml is collected add chloroform only and continue to distill off the chloroform. When it is believed that the amount of chloroform that remains is not great turn off the Variac and allow the flask to cool.

Step 3: Add enough chloroform to bring the total volume to 100 ml. Transfer to a separatory funnel with the stopcock closed. Extract with an equal volume of a saturated sodium bicarbonate solution. Repeat the extraction with sodium bicarbonate and then extract with $H_2O$. Dry over calcium chloride powder. Reassemble the distillation assembly without the reflux column. After adding dry ice to the trap, remove the remaining chloroform under low pressure.

Step 4: Collect and weigh the product.

EXAMPLE 3

Synthesis of Iodine(III)Trifluoroacetate

Step 1: In the hood, pour 14 ml of acetic anhydride into a 250 ml round bottom flask and cool to about −15° C. (dry ice and isopropyl alcohol). While stirring with a magnetic stir bar, carefully add 5.4 ml of red fuming nitric acid (90%, sp. gr. 1.51). Remove the round bottom flask from the dry ice/isopropanol bath. Weigh out 5.0 g iodine and, with the temperature below 20° C., add the iodine to the round bottom flask together with 9.4 ml of trifluoroacetic acid. Stir the mixture for one-half hour. As the iodine dissolves, nitrous oxide is generated and the temperature increases to 40–45° C. If the production of nitrous oxide continues, the iodine is still reacting.

Step 2 If necessary, flush out the remaining nitrous oxide with $N_2$ gas and then set up for low pressure distillation. With the pot temperature below 40° C., reduce the solution to a dark viscous oil of iodine(III)trifluoroacetate.

EXAMPLE 4

Synthesis of Dianisoleiodonoium Trifluoroacetate

Step 1: Dissolve the iodine(III)trifluoroacetate in 30 ml of acetic anhydride. Cool to −10° C. and hold the temperature while adding a solution containing 17.4 ml anisole, 70 ml acetic anhydride, and 10 ml trifluoroacetic acid over 20 minutes. Stopper the flask and store in the refrigerator overnight and then allow 3 hours to come to room temperature.

Step 2: Vacuum distill at the lowest temperature practical. A thick dark oil will remain. Note: Caution must be used when adding to the acid waste from the trap or the receiving flask as the reactive anhydride will rapidly and vigorously react with an aqueous solution. Add diethyl ether to the oil. After approximately 400 ml a precipitate appears.

Step 3: Filter the precipitate and wash with ice cold dry diethyl ether to give the crude dianisoleidonium trifluoroacetate. Recrystallize from toluene to give white feathery needles (mp 134–136° C.). Weigh the product. Save some of the product for NMR, if necessary, or a melting point determination.

EXAMPLE 5

Synthesis of Ethyl-3-(4'-methoxy-3,5-diiodothyro) Propionate

Step 1: Weigh out and combine in a 250 ml round bottom flask 0.1 mole of the ethyl-3-(3,5-diiodo-4-hydroxyphenol) propionate, 50 ml of methanol with 1.5 ml of triethylamine, and 0.1 g of untarnished metallic copper powder. Add 5.9 g of the dianesoleiodonium trifluoroacetate to 70 ml of methanol and then add this mixture to the round bottom flask. A stirring bar is added, the flask stoppered and stirred at room temperature for 24 hours.

Step 2: Filter to remove unreacted copper. Under reduced pressure, remove the methanol to yield a syrup. Dissolve in toluene. Add 1 N HCl and shake for 5 minutes. A large amount of triethylamine will precipitate and must be removed by filtration. Wash the organic layer in the separatory funnel with 10% NaOH and the with $H_2O$. The organic phase is dried over sodium sulfate. Under low pressure the toluene is remove to leave the product.

Step 3: Weigh the product and prepare a sample for NMR and or HPLC analysis.

EXAMPLE 6

Synthesis of DITPA

Step 1: Weigh out 50 g of the coupled product and transfer it to a round bottom flask. Add 100 ml of HI and 100 ml of glacial acetic acid. Blanket with a very slow stream of $CO_2$. Reflux for 5–6 hours and add 100 ml of HI, and reflux overnight.

Step 2: Remove most of the acid with reduced pressure distillation.

Add 200 ml of $H_2O$ and adjust the pH to 5 with 1 N NaOH. The precipitate is collected by filtration. The filtrate is washed with ice cold $H_2O$ and dried under a blanket of $CO_2$.

Step 3: Recrystallize the product from ethanol. Prepare a sample for NMR analysis and melting point determination.

Step 4 Store the final product in a desiccator below 0° C. in a freezer that is locked and has limited access.

Prior to administration to either human patients, or to animals, DITPA may be further compounded with one or more ingredients selected from the group consisting of a carrier, a stabilizer, an excipient, a solubilizer, an antioxidant, a pain-alleviating agent, an isotonic agent, and combinations thereof.

DITPA may be formulated in various ways such as liquid preparations, solid preparations, capsule preparations, implant preparations and the like. DITPA may be formulated for parenteral administration for injection with an appropriate conventional carrier and for oral administration with an appropriate conventional carrier. The formulation for parenteral administration for injection may be prepared by conventional methods known to a person skilled in the art, such as a method comprising the steps of; dissolving DITPA in an appropriate solvent such as sterilized water, buffered solution, isotonic sodium chloride solution and the like; sterilizing by filtration; and filling said solution to a sterilized bottle. An amount of DITPA in the parenteral formulation is from about 0.0002 to about 0.2 (W/V %), and preferred amount is from about 0.001 to about 0.1 (W/V %). The formulation may be prepared by the conventional formulation technique.

DITPA may be administered in the form of inhalation or insufflation. For administration by inhalation or insufflation a DITPA solution is conveniently delivered in the form of an aerosol spray presentation from pressurized packs or nebulizer, with the use of suitable propellants such as carbon dioxide or other suitable gasses. In addition, DITPA may be administered using conventional drug delivery systems well known to a person skilled in the art. Examples of the preparations for drug delivery system are microspheres (nanoparticle, microparticle, microcapsule, bead, liposome, multiple emulsion, etc.) and the like.

A stabilizer may be added to the formulation, and the examples of a stabilizer include albumin, globulin, gelatin, mannitol, glucose, dextran, ethylene glycol and the like. The formulation of the present invention may include a necessary additive such as an excipient, a solubilizer, an antioxidant agent, a pain-alleviating agent, an isotonic agent and the like. The liquid formulation may be stored in frozen condition, or after removal of water by a process such as freeze-drying. The freeze-dried preparations are used by dissolving in pure water for injection and the like before use.

Effective dosages and schedules for administering DITPA may be determined empirically, and such determinations are within the skill in the art. An administration route of the preparation may vary depending on the form of preparation. For example, the parenteral preparation may be administered intravenously, intraarterially, subcutaneously or intramuscularly.

In addition, DITPA may also be formulated for transdermal or implant administration. Such long acting implantation administrations include subcutaneous or intramuscular implantation. Thus, for example, DITPA may be formulated with suitable polymeric or hydrophobic materials (for example as an emulsion in an acceptable oil) or ion exchange resins or as sparing soluble derivatives, for example as a sparingly soluble salt.

Applicants' transdermal delivery system includes a carrier, such as a liquid, gel, solid matrix, or pressure sensitive adhesive, into which DITPA is incorporated. In one embodiment, Applicants' invention does not include a backing material. In an alternative embodiment, Applicants' method includes use of a backing in combination with a carrier. In this embodiment, the portions of the carrier that are not in physical contact with the skin or mucosa are covered with a backing. The backing serves to protect the carrier and the components contained in the carrier, including the DITPA being delivered, from the environment. Backings suitable for use with Applicants' method include metal foils, metalized plastic films, and single layered and multilayered polymeric films.

In one embodiment, Applicants' method comprises transdermal delivery of DITPA dissolved in a solvent system. The solvent system includes water, and optionally one or more lower alcohols such as ethanol, isopropyl alcohol, propyl alcohol, and the like. Preferably, such alcohols have carbon contents between 2 and about 6.

The solvent system may additionally include glycols such as ethylene glycol, propylene glycol, glycerol, and the like. The solvent system may also include one or more dialkylsulfoxides and/or dialkylsulfones. The solvent system may also include one or more ketones, ethers, and esters. Examples include acetone, methylethylketone, dimethylether, diethylether, dibutylether, and alkyl acetates, alkyl proprionates, alkyl butyrates, and the like.

Although solutions of DITPA are preferred, emulsions are also effective. Such emulsions may be aqueous, wherein the aqueous phase is the major and continuous phase, or non-aqueous, wherein a water-insoluble solvent system comprises the continuous phase.

Applicants' method to treat chronic heart failure and/or lower LDL-cholesterol levels using the transdermal delivery of DITPA is effective even without including a substance capable of in vivo stimulation of adenosine 3',5'-cyclic monophosphate, and even without including a substance capable of in vivo stimulation of guanosine 3',5'-cyclic monophosphate. In a separate embodiment of Applicants' invention, substances such as an extract of Coleus Forskholi, may optionally be included in Applicants' transdermal delivery DITPA formulation at a level of between about 0.0001 weight percent to about 1.0 weight percent.

Applicants' transdermal formulation may also contain agents known to accelerate the delivery of medicaments through the skin or mucosa of animals, including humans. These agents are sometimes known as penetration enhancers, accelerants, adjuvants, and sorption promoters, and are collectively referred to herein as "enhancers." Some examples of enhancers include polyhydric alcohols such as dipropylene glycol; oils such as olive oil, squalene, and lanolin; polyethylene glycol ethers and fatty ethers such as cetyl ether and oleyl ether; fatty acid esters such as isopropyl myristate; fatty acid alcohols such as oleyl alcohol; urea and urea derivatives such as allantoin; polar solvents such as dimethyldecylphosphoxide, methyloctylsulfoxide, dimethylacetonide, dimethyllaurylamide, dodecylpyrrolidone, isosorbitol, decylmethylsulfoxide, and dimethylformamide; salicylic acid; benzyl nicotinate; bile salts; higher molecular weight aliphatic surfactants such as lauryl sulfate salts. Other agents include oleic acid and linoleic acids, ascorbic acid, panthenol, butylated hydroxytoluene, tocopherol, tocopheryl acetate, tocopheryl linoleate, propyloleate, isopropyl palmitate, oleamide, polyoxyethylene lauryl ether, polyoxyethylene olelyl ether and polyoxyethylene oleyl ether. In this embodiment, these skin penetration enhancers are present from about 0.01 weight percent to about 5 weight percent.

Applicants' transdermal delivery system of this embodiment can be prepared using conventional methods to apply an appropriate carrier to an appropriate backing. For example, a DITPA-in-adhesive device can be prepared by using the following method; preparing a coating formulation by mixing a solution of the adhesive in a solvent system containing DITPA, and any other desired components, to form a homogeneous solution or suspension; applying the formulation to a substrate such as a backing or a release liner; using well known knife or bar or extrusion die coating methods; drying the coated substrate to remove the solvent; and laminating the exposed surface to a release liner or backing.

The following clinical studies are presented to further illustrate to persons skilled in the art how to make and use Applicants' invention and to identify presently preferred embodiments thereof. These clinical studies are not intended as limitations, however, upon the scope of Applicants' invention, which is defined only by the appended claims.

CLINICAL STUDIES

In clinical trials discussed below wherein DITPA was orally administered to volunteers and patients, the DITPA was mixed under the supervision of a registered pharmacist with lactose and packed into gelatin capsules containing 50 mg of the active ingredient. Identical capsules were packed with lactose to serve as placebo medication.

A dose-ranging study was performed with seven (7) normal volunteers. Study participants comprised men between the ages of 18 and 65 years of age. Before participating in the study, a complete physical examination, electrocardiogram, and echocardiogram were obtained. A complete blood count (CBC), blood chemistries (including liver enzymes and lipids profile), and thyroid function studies (total $T_3$, total $T_4$, free $T_4$, $rT_3$, and thyrotropin) were measured.

On day 1, these normal volunteers were started on 1.875 mg/kg in two divided doses per day. This treatment regimen was continued for two weeks. At the end of the second week, the initial laboratory studies were repeated. The dose was then doubled to 3.75 mg/kg and the volunteers were treated for two additional weeks. At the end of this time physical examination and all laboratory variables again were measured.

Volunteer data were analyzed using Student's paired t-test. Baseline data in DITPA and placebo groups were compared by Student's unpaired t-test. Comparison of placebo and drug treated groups was made by repeated measures ANOVA (SPSS Version 9.5, SPSS Chicago, 11). If P values for drug-time interactions were significant a priori contrasts were performed of the drug-time interaction for two weeks versus baseline. When data were available only at baseline and four week, comparisons were made by difference scores. Baseline values for each participant were subtracted from values after four weeks of treatment and the differences between DITPA and placebo treatments then were compared. P values by two-tailed testing less than 0.05 were considered to be significant.

Table I summarizes the clinical variables following DITPA administrations in normal volunteers. As noted above, seven normal volunteers received DITPA at two dosage levels for two and four weeks.

TABLE I

| | At Baseline | After 2 weeks of treatment | P Value* | After 4 weeks of treatment | P Value+ |
|---|---|---|---|---|---|
| Age | 44.3 ± 3.3 | | | | |
| Weight (kg) | 84.2 ± 2.6 | 83.5 ± 2.6 | 0.08 | 83.6 ± 2.6 | 0.13 |
| Heart Rate (beats/min) | 55.4 ± 2.9 | 58.1 ± 3.2 | 0.93 | 64.3 ± 3.4 | 0.15 |
| Systolic Blood Pressure (mm Hg) | 121.3 ± 4.4 | 122.0 ± 5.4 | 0.86 | 116.3 ± 6.1 | 0.20 |
| Diastolic Blood Pressure (mm Hg) | 77.1 ± 3.5 | 76.1 ± 2.9 | 0.81 | 71.6 ± 3.8 | 0.31 |

Data are means ± SE.
*P values for t-test of baseline vs. 2 week values.
+P values for t-test of baseline vs. 4 week values.

Table II summarizes thyroid hormone measurements after two and four weeks of treatment with DITPA in normal volunteers.

TABLE II

|  | At Baseline | After 2 weeks of treatment | P Values* | After 4 weeks of treatment | P Values+ |
|---|---|---|---|---|---|
| Thyrotropin (mu/L) | 3.53 ± 1.00 | 0.69 ± .38 | 0.04 | 0.44 ± .29 | 0.03 |
| Total $T_4$ ($\mu$g/dL) | 8.73 ± .85 | 5.76 ± .39 | 0.02 | 5.89 ± .44 | 0.04 |
| Free $T_4$ (ng/dL) | 1.04 ± .04 | 0.95 ± .07 | 0.30 | 1.05 ± .06 | 0.94 |
| Total $T_3$ (ng/dL) | 1.06 ± .06 | ND |  | ND |  |
| $rT_3$ (ng/dL) | 23.23 ± 1.71 | 47.41 ± 7.11 | 0.02 | 69.56 ± 9.93 | 0.004 |

Data are means ± SEM for 7 normal volunteers.
ND = Not done
*P values for t-test of baseline vs. 2 week values.
+P values for t-test of baseline vs. 4 week values.

Serum concentrations of thyrotropin, free $T_4$, and $rT_3$ were normal at baseline. After two weeks of administration of the lower dose of the drug (1.875 mg/kg) thyrotropin (P=0.04) and total $T_4$ (P=0.02) were significantly decreased whereas free $T_4$ was unchanged. Serum reverse $T_3$ was significantly increased (P=0.02). Total $T_3$ was not measured after starting the drug because DITPA cross-reacted in the immunoassay.

After two additional weeks of administration at the higher dose (3.75 mg/kg) there was a further decrease in average values for thyrotropin to 0.44±0.29 $\mu$U/ml (P=0.03). These values were at the lower limit of the normal range (0.48 to 4.0 $\mu$U/ml) for the laboratory. All subjects continued their usual activities while receiving the drug and no adverse effects were noted.

The initial phase of Applicants' preliminary study indicated that administration of DITPA to normal volunteers was well tolerated and caused no significant changes in blood pressure and pulse rate at either dose of the drug. In these subjects, echocardiographic parameters were not changed significantly. Thyrotropin levels were decreased at both doses of DITPA administered but plasma $T_4$ remained within the normal range. Total $T_3$ could not be measured during drug administration because DITPA cross-reacted with the anti-$T_3$ antibody. Reverse $T_3$ increased substantially, however. The mechanism for the increase in $rT_3$ is unknown, but may represent competitive inhibition by DITPA of the enzyme 5'-monodeiodinase, which catalyzes the breakdown of $rT_3$ as well as the conversion of $T_4$ to $T_3$. Since no adverse effects were observed in normal volunteers Applicants proceeded with administration of DITPA to a group of individuals with moderately severe heart failure.

After the safety of DITPA was established, clinical trials then demonstrated the efficacy of DITPA to treat chronic heart failure. Patients were eligible for enrollment in these clinical studies if they had symptoms of heart failure and an ejection fraction of less than 35%. Patients were required to be in sinus rhythm. Treatment with digitalis, angiotensin converting enzyme inhibitors, and diuretics were allowed, but β-adrenergic blocking agents were not permitted.

Three patients in the placebo group and one patient receiving DITPA were taking an HMG-CoA reductase inhibitor. Patients were excluded from the study if they were receiving amiodarone, had unstable angina, myocardial infarction within 6 months, significant aortic stenosis, hepatic or renal insufficiency, anemia (hematocrit<30%), pre-existent thyroid disease, sensitivity to iodine, active cancer or any other life-threatening disease.

All patients were hospitalized before initiating treatment and a right heart catheterization, radionuclide ejection fraction and echocardiogram were performed. Serum samples were drawn for measurement of thyrotropin, total $T_4$, free $T_4$, and reverse $T_3$.

DITPA cross-reacted with antibodies for detection of T3, which consequently was not measured. Renal and hepatic function tests also were performed. Patients were randomly assigned in double-blind fashion to receive either DITPA at a dosage of 1.875 mg/kg daily or placebo in two or three divided doses. For the first four days of drug administration patients were monitored on a telemetry unit. Thereafter, weekly electrocardiograms were performed and patients were examined for changes in thyroid or cardiac status or evidence of drug toxicity.

At the end of two weeks an echocardiogram was obtained. If there was no clinical evidence of progression of heart failure or development of an arrhythmia the dose of DITPA was increased to 3.75 mg/kg daily. After an additional two weeks of treatment with the higher dosage of the drug patients were readmitted to the hospital and the tests performed in the initial evaluation were repeated.

M-mode, two-dimensional, and Doppler echocardiograms were obtained with an ultrasonographic system equipped with a 2.5-mHz transducer (GE VingMed, Milwaukee, Wis.) according to the recommendation of the American Society of Echocardiography. Ejection fraction was measured by gated radionuclide myocardial imaging.

Right heart catheterization was performed after the patient had been fasted overnight; no premedication was given. Pulmonary artery, pulmonary capillary wedge and right heart pressures were measured with a 7 Fr Swan-Ganz catheter introduced into the right femoral vein. Blood pressures were recorded with an automated arm cuff system. After an initial stabilization period of 20 to 30 minutes, the resting hemodynamic measurements were obtained. Thermodilution cardiac output measurements were averaged from five recordings after discarding the highest and lowest values. All blood tests were performed in the Clinical Pathology Laboratory at the Southern Arizona Veterans Administration Health Care System.

Twenty-two patients underwent the initial right heart catheterization and were randomized to receive the subject drug or placebo. Nineteen patients completed the study (mean age 61.6, range 47 to 76). Patient functional classes, according to the New York Heart Association classification were II (n=12), III (n=7). One patient had dilated cardiomyopathy. The remaining patients had coronary artery disease, which was considered to be the most likely etiology of congestive heart failure. There was one death in a patient receiving placebo. One patient in the DITPA group was withdrawn because of abdominal pain and subsequently found to have cholelithiasis.

The remaining patients either voluntarily withdrew from the study or were noncompliant. Baseline variables for the two groups were similar, except for ejection fraction, which was lower in the DITPA group. The clinical effects of treatment are shown in Table III.

In the DITPA group, no change in body weight occurred after two weeks of treatment. After 4 weeks there was a decrease of 4 kg while in the placebo group there was an increase in weight, resulting in a borderline statistically significant difference (P=0.059). There were no significant changes in New York Heart Association class or radionuclide ejection fraction. Average systolic and diastolic pressures were decreased, but did not achieve statistical significance.

TABLE III

|  | At Baseline | | P Value* | After 2 weeks of treatment | | After 4 weeks of treatment | | P Value+ |
| --- | --- | --- | --- | --- | --- | --- | --- | --- |
|  | Placebo | DITPA |  | Placebo | DITPA | Placebo | DITPA |  |
| Age | 61.6 ± 2.8 | 61.8 ± 3.3 | 0.97 |  |  |  |  |  |
| Weight (kg) | 85.8 ± 3.6 | 98.7 ± 6.6 | 0.09 | 86.8 ± 10.1 | 98.2 ± 19.3 | 89.4 ± 9.7 | 94.7 ± 18.8 | 0.059 |
| NY Heart Association functional class | 2.2 ± 0.1 | 2.5 ± 0.2 | 0.20 | 2.2 ± 0.1 | 2.4 ± 0.2 | 2.1 ± 0.1 | 2.5 ± 0.2 | 1.00 |
| Radionuclide Ejection Fraction (%) | 28.7 ± 1.9 | 18.1 ± 2.4 | 0.003 |  |  | 29.1 ± 2.8 | 20.6 ± 3.2 | 0.72++ |
| Heart Rate (beats/min) | 76.9 ± 3.4 | 81.3 ± 4.4 | 0.10 | 72.0 ± 5.1 | 83.4 ± 6.5 | 73.9 ± 4.9 | 82.2 ± 4.7 | 0.33 |
| Systolic Blood Pressure (mm Hg) | 114.7 ± 5.0 | 122.8 ± 4.9 | 0.27 | 112.0 ± 4.3 | 116.2 ± 7.4 | 122.8 ± 6.7 | 119.1 ± 6.1 | 0.60 |
| Diastolic Blood Pressure (mm Hg) | 73.5 ± 3.9 | 75.8 ± 4.2 | 0.69 | 66.6 ± 3.1 | 65.7 ± 3.3 | 73.5 ± 5.4 | 66.4 ± 3.6 | 0.11 |

Data are means ± SE for 9 patients receiving DITPA and 10 patients receiving placebo.
*P values for t-test of baseline values of DITPA vs. placebo.
+P values are for ANOVA drug-time interaction.
++P values are for difference scores for baseline vs. 4 weeks.

TABLE IV

|  | At Baseline | | P Value* | After 2 weeks of treatment | | After 4 weeks of treatment | | P Value+ |
| --- | --- | --- | --- | --- | --- | --- | --- | --- |
|  | Placebo | DITPA |  | Placebo | DITPA | Placebo | DITPA |  |
| Cardiac size and shape |  |  |  |  |  |  |  |  |
| LV end-systolic dimension (cm) | 5.64 ± 0.27 | 5.72 ± 0.41 | 0.87 | 5.57 ± 0.33 | 5.87 ± 0.30 | 5.92 ± 0.28 | 6.01 ± 0.33 | 0.85 |
| LV diastolic dimension (cm) | 6.73 ± 0.19 | 6.84 ± 0.33 | 0.78 | 6.81 ± 0.26 | 6.83 ± 0.35 | 7.00 ± 023 | 6.96 ± 0.30 | 0.71 |
| LV mass (g) | 492.7 ± 73.3 | 495.8 ± 45.9 | 0.97 | 429.4 ± 37.2 | 474.2 ± 38.2 | 461.7 ± 32.9 | 477.9 ± 40.5 | 0.75 |
| Systolic Function |  |  |  |  |  |  |  |  |
| Fractional shortening (%) | 16.7 ± 2.1 | 17.0 ± 3.5 | 0.95 | 18.6 ± 2.5 | 13.8 ± 2.4 | 15.5 ± 2.0 | 13.8 ± 2.5 | 0.39 |
| Shortening velocity (circ/sec) | 0.64 ± 0.07 | 0.69 ± 0.15 | 0.74 | 0.67 ± 0.07 | 0.55 ± 0.09 | 0.58 ± 0.07 | 0.57 ± 0.10 | 0.49 |
| Diastolic Function |  |  |  |  |  |  |  |  |
| Isovolumic relaxation time (msec) | 94.0 ± 7.0 | 92.2 ± 9.5 | 0.88 | 107.7 ± 7.8 | 87.5 ± 9.2++ | 109.0 ± 8.2 | 84.4 ± 8.5 | 0.045 |
| Ratio of early to late filling | 1.08 ± 0.16 | 1.10 ± 0.21 | 0.97 | 1.05 ± 0.15 | 0.89 ± 0.17 | 1.08 ± 0.18 | 1.16 ± 0.26 | 0.56 |

Data are means ± SE for 9 patients receiving DITPA and 10 patients receiving placebo.
*P values are for t-test of baseline values for DITPA vs. placebo groups.
+P values are for ANOVA drug-time interaction.
++ANOVA contrast for baseline to 2 weeks P = 0.051.

Echocardiographic data are shown in Table IV. DITPA produced no significant changes in ventricular mass or size after two weeks or four weeks of treatment. Indices of systolic function, such as fractional shortening and the velocity of circumferential fiber shortening were unchanged. However, isovolumetric relaxation time, a measure of active diastolic relaxation, was decreased significantly after two weeks (P=0.05) and four weeks of treatment (P=0.045). The ratio of early to late diastolic ventricular filling was unchanged.

four weeks of treatment with DITPA there were no effects on heart rate, pulmonary arterial or right atrial pressures. However, the group averages for resting cardiac outputs and cardiac indices in those receiving DITPA were increased significantly compared to placebo treatment (P=0.07 and P=0.02, respectively). This was accompanied by a decrease in systemic vascular resistance index for the DITPA group (P=0.02). By contrast, cardiac output, cardiac index and

TABLE V

| Variable | At Baseline | | P Value* | After 4 weeks of treatment | | P Value+ |
|---|---|---|---|---|---|---|
| | Placebo | DITPA | | Placebo | DITPA | |
| Heart Rate | 73.4 ± 5.0 | 84.8 ± 4.9 | 0.12 | 72.0 ± 6.3 | 89.6 ± 5.3 | 0.16 |
| Pulmonary artery pressures (mm Hg) | | | | | | |
| Systolic | 42.4 ± 4.2 | 45.0 ± 6.2 | 0.72 | 44.9 ± 6.4 | 49.1 ± 5.3 | 0.80 |
| Diastolic | 20.9 ± 3.0 | 25.1 ± 4.1 | 0.41 | 22.2 ± 3.0 | 25.4 ± 2.5 | 0.94 |
| Mean | 28.9 ± 3.3 | 30.1 ± 5.0 | 0.84 | 30.1 ± 3.9 | 33.4 ± 3.2 | 0.61 |
| Wedge | 18.0 ± 2.5 | 24.0 ± 3.9 | 0.20 | 21.1 ± 3.2 | 21.8 ± 2.75 | 0.13 |
| Right atrial pressure (mm Hg) | 9.9 ± 1.7 | 8.1 ± 1.7 | 0.47 | 10.7 ± 1.4 | 10.5 ± 1.8 | 0.36 |
| Cardiac Output (liters/min) | 5.06 ± 0.36 | 4.50 ± 0.36 | 0.30 | 4.98 ± 0.25 | 5.30 ± 0.36 | 0.07 |
| Cardiac Index (liters/min/m$^2$) | 2.51 ± 0.17 | 2.10 ± 0.14 | 0.09 | 2.44 ± 0.11 | 2.54 ± 0.16 | 0.04 |
| Mean Arterial Pressure (mm Hg) | 91.4 ± 3.3 | 96.2 ± 6.7 | 0.51 | 92.0 ± 4.1 | 92.0 ± 5.7 | 0.44 |
| Systemic Vascular Resistance (dynes x sec x cm$^{-5}$) | 2,685 ± 165 | 3,465 ± 319 | 0.04 | 2,700 ± 159 | 2,644 ± 257 | 0.02 |

Data are means ± SE for 9 patients receiving DITPA and 10 patients receiving placebo.
*P values are for t-test of baseline values for DITPA vs. placebo groups.
+P values are for difference scores for DITPA vs. placebo groups at 4 weeks.

The effects of treatment with DITPA on hemodynamic variables measured invasively are shown in Table V. After peripheral resistance were unchanged after four weeks of placebo administration.

TABLE VI

| | At Baseline | | P Value* | After 2 weeks of treatment | | After 4 weeks of treatment | | P Value+ |
|---|---|---|---|---|---|---|---|---|
| | Placebo | DITPA | | Placebo | DITPA | Placebo | DITPA | |
| Thyrotropin (mU/L) | 1.65 ± 0.2 | 2.47 ± 0.6 | 0.17 | 1.85 ± 0.3 | 0.04 ± 01++ | 2.13 ± 0.3 | 0.018 ± 0.0004 | <0.001 |
| FreeT4 (ng/dL) | 1.19 ± 0.1 | 1.19 ± 0.1 | 0.96 | 1.18 ± 0.08 | 1.17 ± 0.1 | 1.12 ± 0.1 | 1.17 ± 0.15 | 0.72 |
| ReverseT3 (ng/dL) | 236 ± 23 | 197 ± 27 | 0.29 | 207 ± 15 | 477 ± 83++ | 237 ± 61 | 559 ± 108 | 0.002 |
| Cholesterol (ng/dL) | 183.0 ± 10.5 | 198.9 ± 19.7 | 0.49 | 198.7 ± 10.4 | 160.6 ± 14.3++ | 181.9 ± 12.3 | 140.7 ± 16.2 | 0.013 |
| LDL Cholesterol (ng/dL) | 117.9 ± 7.5 | 115.8 ± 15.8 | 0.91 | 122.5 ± 10.3 | 89.4 ± 12.7 | 106.1 ± 10.2 | 80.5 ± 13.7 | 0.235 |
| HDL Cholesterol (mg/dL) | 32.4 ± 2.9 | 32.8 ± 2.8 | 0.94 | 36 ± 3.2 | 30.6 ± 2.0 | 34.8 ± 5.0 | 31.4 ± 3.1 | 0.055 |
| Triglyceride (mg/dL) | 163.4 ± 29.2 | 248.7 ± 40.4 | 0.11 | 218.7 ± 40.2 | 203.0 ± 30.4++ | 204.3 ± 53.9 | 143.7 ± 21.1 | 0.005 |

Data are means ± SE for 9 patients receiving DITPA and 10 patients receiving placebo.
*P values are for t-test of baseline values for DITPA vs. placebo groups.
+P values are for ANOVA drug-time interactions.
++ANOVA contrasts for baseline values vs. 2 weeks of treatment P < 0.05.

As shown in Table VI, serum concentrations of thyrotropin, free $T_4$, and $rT_3$ were not significantly different at baseline in the treatment and control group. Values for thyrotropin and free $T_4$ were within the normal range whereas $rT_3$ values were elevated at baseline in both groups. After two weeks there was a highly significant decrease in thyrotropin levels in patients receiving DITPA, which became more pronounced after four weeks of treatment. In the placebo group, thyrotropin was unchanged at both times. Interestingly, treatment with DITPA did not cause significant changes in free $T_4$. However, $rT_3$ progressively increased after two and four weeks of treatment.

The effects of DITPA and placebo on serum lipid levels also are shown in Table VI. After two weeks of treatment with DITPA there was a significant decrease in value of cholesterol for the group from 185.8±46.9 mg/dL at baseline to 160.6±14.3 mg/dL (P<0.05). After four weeks of DITPA treatment there was a further decrease to 140.7±16.2 mg/dL (P=0.013). LDL-cholesterol decreased from 107.3±42.8 mg/dL at baseline to 89.4±12.7 at two weeks and 80.5±13.7 mg/dL after 4 weeks. Although LDL-cholesterol decreased in 8 of 9 patients treated for 4 weeks there was variability in the magnitude of the response and the ANOVA value did not achieve statistical significance (P=0.235). HDL-cholesterol trended down with DITPA treatment but did not achieve statistical significance. Serum triglycerides were elevated at baseline in the DITPA treatment group and decreased by 11% after two weeks of treatment (P<0.05) and 35% after four weeks (P=0.005). None of these changes in serum lipids were observed in patients receiving placebo.

Thyroid hormone replacement in hypothyroidism is thought to lower cholesterol by increasing the activity of LDL-cholesterol receptors and lipoprotein lipase. DITPA, however, has never previously been clinically tested for its cholesterol lowering activity. After two weeks in the group receiving DITPA there was an average decrease in cholesterol and LDL-cholesterol of 14% and 17%, respectively. After four weeks of treatment cholesterol and LDL-cholesterol were decreased by 24% and 25%, respectively.

Values for serum triglycerides, which were elevated at baseline in both groups, were decreased after two and four weeks of treatment with DITPA. Given the large number of patients with heart failure secondary coronary artery disease, the lipid lowering effects of DITPA is a potentially useful attribute of the drug.

The major hemodynamic effects of DITPA in heart failure patients were an increase in cardiac index and lower systemic vascular resistance. These changes occurred without an increase in resting heart rate. At baseline the gated radionuclide ejection fractions were smaller in the DITPA treatment group than the placebo group and did not change significantly during the study. Judging by the unchanged ejection fraction and echocardiographic parameters of systolic function, LV systolic function probably was unaffected by treatment with DITPA. However, there was almost uniform improvement in diastolic function as assessed by shortening of isovolumic relaxation time. Interestingly, echocardiographic changes were not seen in normal volunteers suggesting that DITPA treatment improves depressed cardiac function, but does not stimulate cardiac performance in the normal heart.

Because of experimental indications that DITPA causes less metabolic response than thyroid hormone and was well tolerated in normal subjects, patients with ischemic heart disease were enrolled in the present trial. The drug also was well tolerated in this group of patients. No arrhythmias were noted. There was no increase in frequency or severity of anginal attacks and clinical manifestations of hyperthyroidism were not observed.

While the invention has been described in detail herein in accordance with certain preferred embodiments thereof, many modifications and changes therein my be effected by those skilled in the art. Accordingly, it is intended by the appended claims to cover all such modifications and changes as fall within the true spirit and scope of the invention.

We claim:

1. A method for treatment of a human patient with congestive heart failure, comprising administering to the human patient a therapeutically effective amount of 3,5-diiodothyropropionic acid.

2. The method of claim 1, wherein 3,5-diiodothyropropionic acid is administered as a formulation selected from the group consisting of a liquid preparation, solid preparation, capsule preparation, and an implant preparation.

3. The method of claim 2, wherein said formulation further comprises a pharmaceutically acceptable carrier.

4. The method of claim 3, wherein said formulation further comprises at least one of a stabilizer, excipient, solubilizer, antioxidant, pain-alleviating agent, and an isotonic agent.

5. The method of claim 1, wherein said 3,5-diiodothyropropionic acid is administered by patenteral injection.

6. The method of claim 1, wherein said 3,5-diiodothyropropionic acid is administered by patenteral intravenous injection.

7. The method of claim 1, wherein said 3,5-diiodothyropropionic acid is administered orally.

8. The method of claim 1, wherein said 3,5-diiodothyropropionic acid is administered directly into the pulmonary system of the patient.

9. The method of claim 1, wherein said 3,5-diiodothyropropionic acid is administered transdermally.

10. The method of claim 1, wherein said 3,5-diiodothyropropionic acid is administered by implantation.

11. A method to lower cholesterol blood levels of a patient, comprising administering to the patient a therapeutically effective amount of 3,5-diiodothyropropionic acid.

12. The method of claim 11, wherein 3,5-diiodothyropropionic acid is administered as a formulation selected from the group consisting of a liquid preparation, solid preparation, capsule preparation, and an implant preparation.

13. The method of claim 12, wherein said formulation further comprises a pharmaceutically acceptable carrier.

14. The method of claim 13, wherein said formulation further comprises at least one of a stabilizer, excipient, solubilizer, antioxidant, pain-alleviating agent, and an isotonic agent.

15. The method of claim 11, wherein said 3,5-diiodothyropropionic acid is administered by patenteral injection.

16. The method of claim 11, wherein said 3,5-diiodothyropropionic acid is administered by patenteral intravenous injection.

17. The method of claim 11, wherein said 3,5-diiodothyropropionic acid is administered orally.

18. The method of claim 11, wherein said 3,5-diiodothyropropionic acid is administered directly into the pulmonary system of the patient.

19. The method of claim 11, wherein said 3,5-diiodothyropropionic acid is administered transdermally.

20. The method of claim 11, wherein said 3,5-diiodothyropropionic acid is administered by implantation.

* * * * *